(12) United States Patent
Nakamura et al.

(10) Patent No.: US 6,386,045 B1
(45) Date of Patent: May 14, 2002

(54) DYNAMIC VISCOELASTICITY MEASURING SYSTEM

(75) Inventors: Toshihiko Nakamura; Nobutaka Nakamura, both of Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/670,654

(22) Filed: Sep. 27, 2000

(30) Foreign Application Priority Data

Sep. 28, 1999 (JP) .......................................... 11-274733

(51) Int. Cl.$^7$ ................................................ G01N 3/00
(52) U.S. Cl. .......................................... 73/805; 73/760
(58) Field of Search ...................... 73/787, 788, 789, 73/794, 804, 805, 841, 760

(56) References Cited

U.S. PATENT DOCUMENTS

| | | | | |
|---|---|---|---|---|
| 4,777,599 A | * | 10/1988 | Dorogi et al. ......... | 364/413.02 |
| 5,253,513 A | * | 10/1993 | Van Arsdale et al. ...... | 73/54.41 |
| 5,303,578 A | * | 4/1994 | Williams et al. ........... | 73/54.24 |
| 5,959,215 A | * | 9/1999 | Ono et al. .................... | 73/798 |
| 6,005,400 A | * | 12/1999 | Thundat et al. ............. | 324/752 |

* cited by examiner

Primary Examiner—Max Noori
(74) Attorney, Agent, or Firm—Adams & Wilks

(57) ABSTRACT

In bending type or shearing type dynamic viscoelasticity measurement, a static stress adjuster adjusts static stress to zero in order to effectively eliminate static stress caused by influences such as warp caused by thermal expansion of a specimen or residual stress, for instance. Further, a static distortion adjuster adjusts a varying speed of static distortion to zero in order to suppress an increase of the static distortion and prevent the specimen from being excessively distorted even when the specimen is soft and has little restoring force. A dynamic viscoelasticity measuring system includes the static distortion adjuster for adjusting the static distortion of the specimen and the static stress adjuster for adjusting the static stress of the specimen, and measures the viscoelasticity of the specimen by selective operation or cooperation of the static distortion adjuster and the static stress adjuster depending upon quality change of the specimen being measured.

6 Claims, 2 Drawing Sheets

DYNAMIC VISCOELASTICITY MEASURING SYSTEM

BACKGROUND OF THE INVENTION

The present invention relates to a dynamic viscoelasticity measuring system which measures viscoelasticity of a material as functions of time, temperature and frequency.

The following are examples of existing viscoelasticity measuring systems: the dynamic viscoelasticity measuring system of Japanese Patent No. 2756492; the tension type viscoelasticity measuring system of Japanese Patent No. 2767634; and the viscoelasticity measuring system of Japanese Patent Laid-Open Publication No. Hei 11-218483.

The dynamic viscoelasticity measuring system disclosed in Japanese Patent No. 2756492 (called "Reference 1" hereinafter) includes a moving mechanism for moving an electromagnetic force generator which generates AC stress to be applied to a specimen, and eliminates offset from a sine wave distortion signal. This measuring system can effectively and reliably obtain a distortion signal which is free from offset caused by thermal expansion of the specimen and a creep phenomenon and has only amplitude.

In the dynamic viscoelasticity measuring system of Japanese Patent No. 2767634 (called "Reference 2" hereinafter), the offset of the sine wave distortion signal is eliminated using the moving mechanism of Reference 1 in order to perform the tension-type dynamic viscoelasticity measurement. Further, in order to quickly eliminate variations of static stress caused by thermal expansion or softening of the specimen, this measuring system includes the circuit designed taking the elasticity of the plate spring as the probe support into consideration. Therefore, the measuring system can prevent the moving mechansim from being very frequently moved, quickly adjust DC force, and continuously provide the specimen with tension serving as optimum static stress.

The Reference 1 and 2 are aimed at effectively and reliably measuring the distortion signal. When the moving mechanism is moved in order to eliminate offset from the sine wave distortion signal to be measured by the displacement detecting circuit, static distortion and static stress of the specimen vary as described hereinafter. With respect to the static distortion, the center of the sine wave distortion signal is displaced compared with that at the initial position thereof, so that the specimen is subject to the static distortion in accordance with a moving amount of the moving mechanism. On the other hand, since the moving mechanism is moved in accordance with the deformation of the specimen, the elasticity of the plate spring applied to the specimen from the measuring system does not vary, and the static stress of the specimen also remains invariable.

In other words, it is understood that the structure for eliminating the offset from the sine wave distortion signal is designed so as to move the moving mechanism in accordance with the deformation of the specimen and to adjust the static stress of the specimen using a static stress adjustor which maintains the static stress of the specimen at a certain value.

The viscoelasticity measuring system of Japanese Patent Laid-Open Publication No. Hei 11-218483 (called "Reference 3" hereinafter)is the static and dynamic viscoelasticity measurement system which performs two types of static viscoelasticity measurement, i.e. stress relaxation measurement by the static distortion adjuster, and creep measurement by the static stress adjustor. An operator selectively operates the static distortion adjuster or the static stress adjuster for each measurement.

However, when the References 1 and 2 in which the static stress of the specimen is adjusted using the static stress adjuster where the moving mechanism is moved in accordance with the deformation of the specimen is applied to the dynamic viscoelasticity measurement of bending type or shearing type, there are the following problems.

In the bending or shearing type dynamic viscoelasticity measurement, the specimen is preferably free from static distortion. If the moving mechanism is extensively moved and the static distortion is increased, displacement is caused between a specimen chuck and a fixedly attached specimen holder. For example, in the case of the bending type viscoelasticity measurement, the deformation center plane with respect to the bending deformation of the specimen is also distorted, so that the specimen deviates from the ideal bending deformation, which would lead to inaccurate dynamic viscoelasticity measurement.

In actual measurement, the specimen chuck tends to be slightly displaced because of warp caused by the thermal expansion of the specimen and residual stress, thereby resulting in offset in the distortion signal. In such a case, the moving mechanism is slightly moved based on the References 1 and 2 in order to maintain the bending distortion approximately equal to the ideal bending distortion and perform correction. Provided that the specimen is stiff to a certain degree and has restoring force against DC force, the References 1 and 2 can effectively allow fine correction.

However, if the specimen becomes very soft due to temperature variations or the like, it tends to creep and has only small restoring force. In this state, if the References 1 and 2 are applied, finite distortion signals, which are generated by creep due to a slight amount of DC force applied to the specimen before or during the movement of the moving mechanism and due to deviation of slight mechanical offset remaining between the distortion sensor and probe or the like, are repeatedly corrected. Especially, in the case of the bending type viscoelasticity measurement, the DC force may cause extensive deformation compared with the case where the tension type viscoelasticity measurement is performed and the DC force is the same. As a result, the offset of the distortion signal and moving amount of the moving mechanism are increased, and the specimen coupled to the moving mechanism via the specimen chuck continues its deformation. Further, since the specimen has small restoring force, it seldom returns to its initial position. In lengthy measurement, correction is repeated, so that the moving amount of the moving mechanism will be accumulated. The specimen will be subject to distortion which cannot be considered to be caused by the bending or shearing deformation.

Therefore, it is impossible to precisely perform the dynamic viscoelasticity measurement.

The Reference 3 relates to the static viscoelasticity measurement but not to the dynamic viscoelasticity measurement. Further, the operator selectively operates the static distortion adjuster or the static stress adjuster each time measurement is performed. Even if the quality of the specimen changes due to temperature variations or the like during the measurement, selective operation or cooperation of the static distortion adjuster and the static stress adjuster is not carried out in response to the quality change of the specimen. Therefore, even when the foregoing adjusters are independently operated for the dynamic viscoelastricity measurement, the following problems will occur. Specifically, when the static distortion adjuster is utilized, the warp caused by the thermal expansion of the specimen and the residual stress if forcibly suppressed, so that excessive static stress will be applied to the specimen. On the other hand, when the static stress adjuster is used, the specimen will be excessively distorted as described above.

SUMMARY OF THE INVENTION

In order to overcome the foregoing problems of the related art, the invention is intended to provide a dynamic viscoelasticity measuring system for measuring viscoelasticity of a specimen on the basis of the relationship between AC stress and AC distortion occuring in the specimen, comprising a static distortion adjuster for adjusting static distortion generated in the specimen and a static stress adjuster for adjusting static stress generated in the specimen, wherein either the static distortion adjuster or the static stress adjuster is selectively operated, or both of the static distortion adjuster and the static stress adjuster are made to cooperate, depending upon quality changes of the specimen being measured. Even when the specimen is very stiff or soft, it is possible to optimally adjust the static distortion and the static stress in accordance with quality changes of the specimen. Further, the moving amount of the moving mechanism can be maintained at an appropriate value.

The dynamic viscoelasticity measuring system of the invention operates as follows.

With the bending or shearing type dynamic viscoelasticity measurement, when the specimen is stiff and has sufficient restoring force, i.e. when an amplitude ratio of AC stress to AC distortion detected by a distortion sensor is large enough, the References 1 and 2 will be applied in order to eliminate influences such as warping caused by the thermal expansion of the specimen and the residual stress. For instance, when the amplitude ratio is larger than a predetermined maximum value, the static stress adjuster will be used to adjust the DC force applied to the specimen to zero. Further, the moving mechanism will be effectively moved in order to precisely perform the dynamic viscoelasticity measurement.

If the specimen becomes too soft due to temperature variation and so on, i.e. when the amplitude radio of the AC force to the AC distortion detected by the distortion sensor is sufficiently small, influences such as deformation stress caused by the thermal expansion of the specimen and residual stress are negligible. For instance, when the amplitude ratio is below a predetermined minimum value, the static distortion adjuster will be operated in order to stop the moving mechanism, reduce a varying speed of the static distortion to zero, and apply slight DC force to the specimen, thereby reducing the offset of the distortion signal to zero.

In accordance with the invention, the dynamic viscoelasticity measuring system measures the viscoelasticity by selectively operating the static distortion adjuster or the static stress adjuster. If the dynamic viscoelasticity measurement is performed by cooperation of these adjusters, it is possible to eliminate influences such as the warp caused by the thermal expansion of the specimen and the residual stress, and to maintain the moving mechanism at its intial position if the specimen has little restoring force. Further, the specimen is protected against excessive distortion, and can maintain ideal bending or shearing distortion.

DETAILED DESCRIPTION OF THE PREFERRED EMBODIMENT

The invention will be described with reference to the preferred embodiment.

Figure 1:
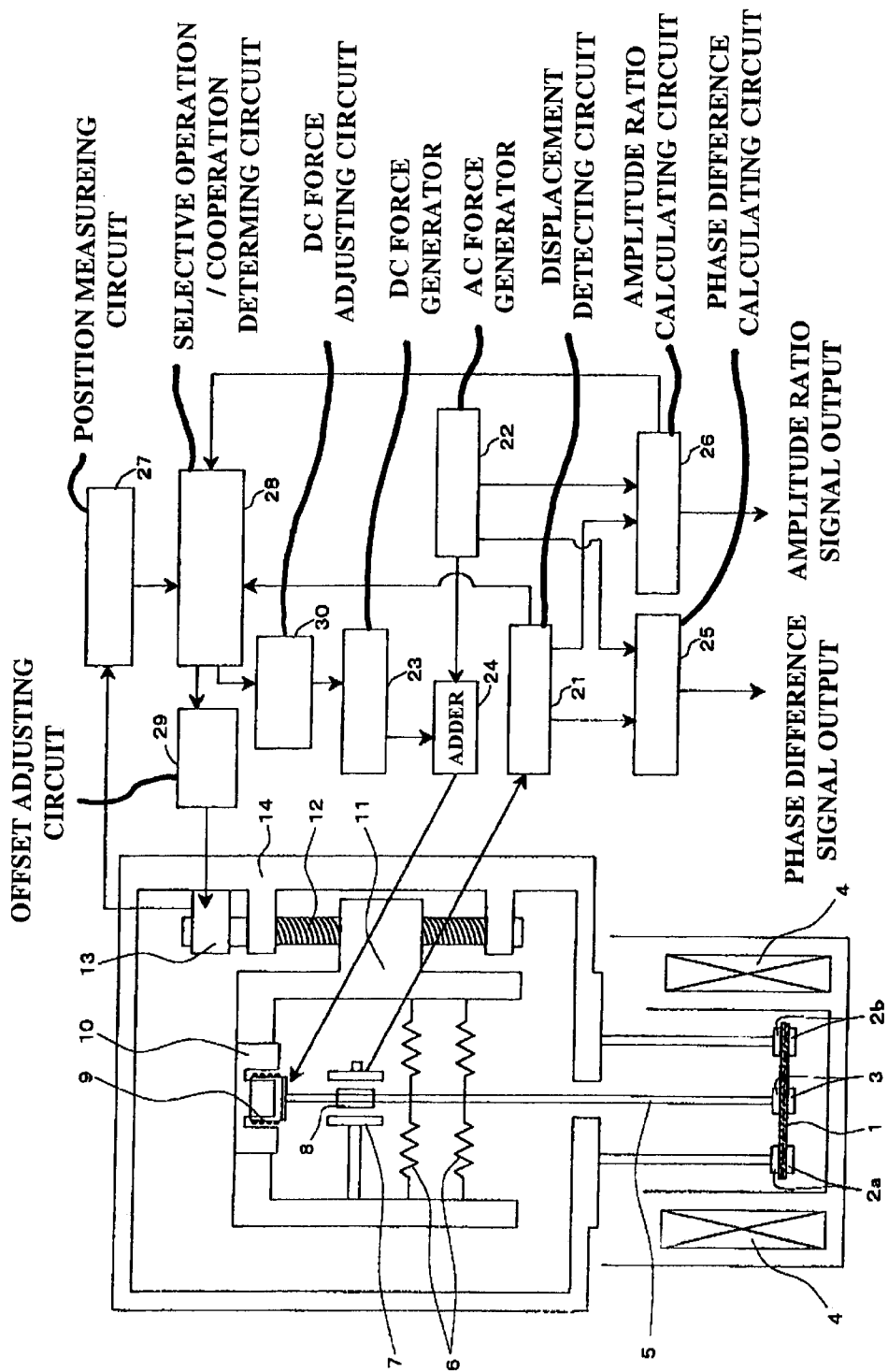
FIG. 1 is a sectional view of a dynamic viscoelasticity measuring system according to one embodiment of the invention, and a block diagarm thereof.

Referring to FIG. 1, reference numeral 1 denotes a plate-shaped specimen subject to bending type viscoelasticity measurement. The bending center plane of bending distortion is shown by a chained line. The bending center plane is present at the center along the thickness of the specimen, and its vertical to the plane of the drawing sheet. Left and right specimen holders 2a and 2b for the bending measurement are fixedly attached to a body 14 so that they are very rigid in the vertical direction. Reference numeral 3 denotes a specimen chuck. The specimen holders 2a and 2b are indirectly coupled via the specimen 1 so that they do not adversely affect viscoelasticity measurement of the specimen 1. Since FIG. 1 shows one embodiment of the invention, the specimen, specimen holders and specimen chuck are described as typical components. According to the invention, the specimen chuck 3 can be maintained substantially near its initial position with respect to the specimen 1, so that the deformation center plane of the bending deformation may deviate as little as possible. Therefore, the invention is also effectively applicable to a cantilever bending type or shearing type dynamic visoelasticity measurement where a deformation center plane similar to that in the bending type measurement is present.

A cylindrical furnace 4 heats or cools an area around the specimen 1 in order to adjust a temperature of the specimen 1. A temperature controller, not shown, varies the temperature of the specimen 1 to a desired value. Reference numeral 5 denotes a metal probe which is thin and rigid, and is connected to the specimen chuck 3 via one end thereof. A pair of metal springs 6 are fixedly attached to a moving mechanism holding member 11 to support the probe 5, and elastically support the plate springs 6. The plate springs 6 control resilient movement of the probe 5 along the length thereof. In FIG. 1, the plate springs 6 are depicted in a zigzag shape in order to show that they are springs. The plate springs 6 are actually disc springs having ventilating holes therein. A cylindrical differential transformer 7 is fixedly attached to the moving mechanism holding member 11. A core is attached to a part of the probe 5 and is surrounded by the differential transformer 7. In response to electromagnetic and relative operation between the differential transformer 7 and the core 8, a variation of relative positions of the probe 5 and the differential transformer 7 is output as an electric signal.

Reference numeral 9 denotes a coil fixedly attached to one end of the probe 5. The coil 9 is surrounded by a permanent magnet 10 which is fixedly attached to the moving mechanism holding member 11 to be described later, and applies AC force and DC force to the probe 5 because of the electromagnetic relative operation. Both the AC and DC forces are applied to the specimen 1 via the specimen chuck 3. The coil 9 and permanent coil 10 constitute an electromagnetic force generator.

The moving mechanism holding member 11 firmly holds the disc springs 6, differential transformer 7 and permanent magnet 10, and is movably fixed to a ball screw 12 using a bearing, not shown. Referring to FIG. 1, the moving mechanism holding member 11 (called the "holding member 11" hereafter) is movable up and down along the length of the probe 5, moves step by step, stops during the viscoelasticity measurement, and then moves step by step. In other words, the holding member 11 repeats its step-by-step movement.

The ball screw 12 is fixed on a body 14 using a bearing (not shown), is coupled to a stepping motor 13, and moves the holding member 11 in response to the rotation of the stepping motor 13. The body is fixed to a test bench or the like (not shown) in such a manner that the probe 5 is vertical, and the specimen chuck 3 is at a lower position as shown in FIG. 1. Alternatively, the body 14 may be inverted such that the specimen chuck 3 is at the upper position and the probe 5 is horizontal. Further, the body 14 supports the specimen holders 2a and 2b so that they are fixed, as described above.

A displacement detecting circuit 21 detects an electric signal from the differential transformer 7 as a distortion signal from the specimen 1. An AC force generator 22 electrically generates AC force to be applied to the specimen 1. A DC force generator 23 electrically generates DC force to be applied to the specimen 1. An adder 24 electrically synthesizes the AC and DC forces, and provides an electric outputs to the coil 9. The coil 9 generates electromagnetic force, which is supplied to the specimen 1 as dynamic force.

A phase difference detecting circuit 25 compares the AC force generated by the AC force generator 22 with the AC distortion of the specimen 1 detected by the displacement detecting circuit 21, and detects and outputs a phase difference. An amplitude ratio calculating circuit 26 compares the AC force generated by the AC force generator 22 with the AC distortion of the specimen 1 detected by the displacement detecting circuit 21, and calculates and outputs a ratio of an AC force amplitude to a distortion amplitude. The output phase difference and amplitude ratio are transmitted to a station constituted by computers (not shown), and are analyzed as viscoelasticity data of the specimen 1.

A position measuring circuit 27 measures a position of the moving mechanism holding member 11 on the basis of rotation angle data of the stepping motor 13, and outputs a signal representative of static distortion of the specimen 1. In order to accurately measure the static distortion of the specimen 1, it is necessary to evaluate both a moving amount of the moving mechanism holding member 11 and the distortion signal from the displacement detecting circuit 21. However, the distortion signal from the displacement detecting circuit 21 is controlled to be a minute value in the order of several micrometers by either an offset adjusting circuit 29 for realizing the functions of the References 1 and 2 or a DC force adjusting circuit 30 (to be described later). Therefore, the distortion signal is approximately between several ten micrometers and several millimeters, so that the distortion signal of the displacement detecting circuit 21 may be disregarded when measuring the static distortion which is larger than the AC distortion or offset.

A selective operation/cooperation determining circuit 28 determines selective operation or cooperation of the static distortion adjuster and the static stress adjuster in accordance with the amplitude ratio output from the amplitude ratio calculating circuit 26 and the static distortion output from the position measuring circuit 27. Specifically, the selective operation/cooperation determining circuit 28 (called the "circuit 28") determines whether either the static distortion adjuster or the static stress adjuster should be selectively operated, or whether these adjusters should cooperate, on the basis of the ratio of the AC force amplitude (out put from the amplitude ratio calculating circuit 26) to the distortion amplitude (output by the amplitude ratio calculating circuit 26), or on the basis of a varying speed of static distortion derived by time-differentiating the static distortion from by the position measuring circuit 27. The circuit 28 sends adjustment instruction to the offset adjusting circuit 29 and DC force adjusting circuit 30 on the basis of the determined result.

The offset adjusting circuit 29 outputs a signal in order to effectively move the holding member 11, thereby accomplishing the functions of the References 1 and 2. When adjusting the static stress, the offset adjusting circuit 29 functions as described in the References 1 and 2. In order to adjust the static distortion, the offset adjusting circuit 29 keeps on outputting a signal for immobilizing the holding member 11.

The DC force adjusting circuit 30 instructs the DC force generator 23 to generate an appropriate output. When adjusting the static stress, the DC force adjusting circuit 30 instructs the generation of constant DC force while, when adjusting the static distortion, the DC force adjusting circuit 30 instructs the generation of DC force in order to reduce an output of the displacement detecting circuit 21 to zero.

The circuit 28 operates as described hereinafter. If the specimen is stiff and has sufficient restoring force, i.e. if the amplitude ratio is large enough, the inventions of the References 1 and 2 are applied, thereby eliminating influences such as the warp caused by the thermal expansion of the specimen or the residual stress. It is assumed here that the amplitude ratio is larger than the maximum value, e.g. it is larger than approximately a total of spring constants of the two disc springs 6. The circuit 28 provides the output of the displacement detecting circuit 21 as it is to the offset adjusting circuit 29, and instructs to effectively move the holding member 11 in order that the viscoelasticity of the specimen is reliably and precisely measured. Further, the circuit 28 orders the DC force adjusting circuit 30 to adjust the DC force applied to the specimen 1 to zero. In this state, the static distortion generated in the specimen 1 remains as it is, which means that the static distortion is not adjusted. On the other hand, the static stress generated in the specimen 1 is a certain value since no DC force is applied to the specimen 1. Therefore, the circuit 28, the offset adjusting circuit 29 and the DC force adjusting circuit 30 function as the static stress adjuster, thereby adjusting the static stress of the specimen 1 to a certain value.

In the foregoing state, no DC force is applied to the specimen. In the case shown in FIG. 1, the probe 5 is vertical, so that gravity equivalent to a mass of the probe 5, coil 9 and specimen chuck 3 acts downwards. The electromagnetic force generator constituted by the coil 9 and permanent coil 10 also generates upward DC force sufficient to offset the gravity.

If the specimen becomes very soft due to temperature variation or the like, i.e. if the amplitude ratio is very small, it is possible to disregard influences of deformation stress such as the warp of the specimen 1 caused by the thermal expansion or the residual stress. It is assumed here that the amplitude ratio is less than a given minimum value which is slightly smaller than the maximum value, for example. The circuit 28 disregards the output of the displacement detecting circuit 21 does not provide any output to the offset adjusting circuit 29, stops the moving mechanism, and orders the DC force adjusting circuit 30 to apply a small DC force to the specimen 1, thereby maintaining the offset of the distortion signal at zero. In this state, the static distortion of the specimen 1 is adjusted to a certain value since the moving mechanism stays at its position. On the other hand, the static stress of the specimen 1 remains as it is. This means that the circuit 28, offset adjusting circuit 29 and DC force adjusting circuit 30 function as the static distortion adjuster in order to keep the static distortion of the specimen 1 at a certain value.

Figure 2:
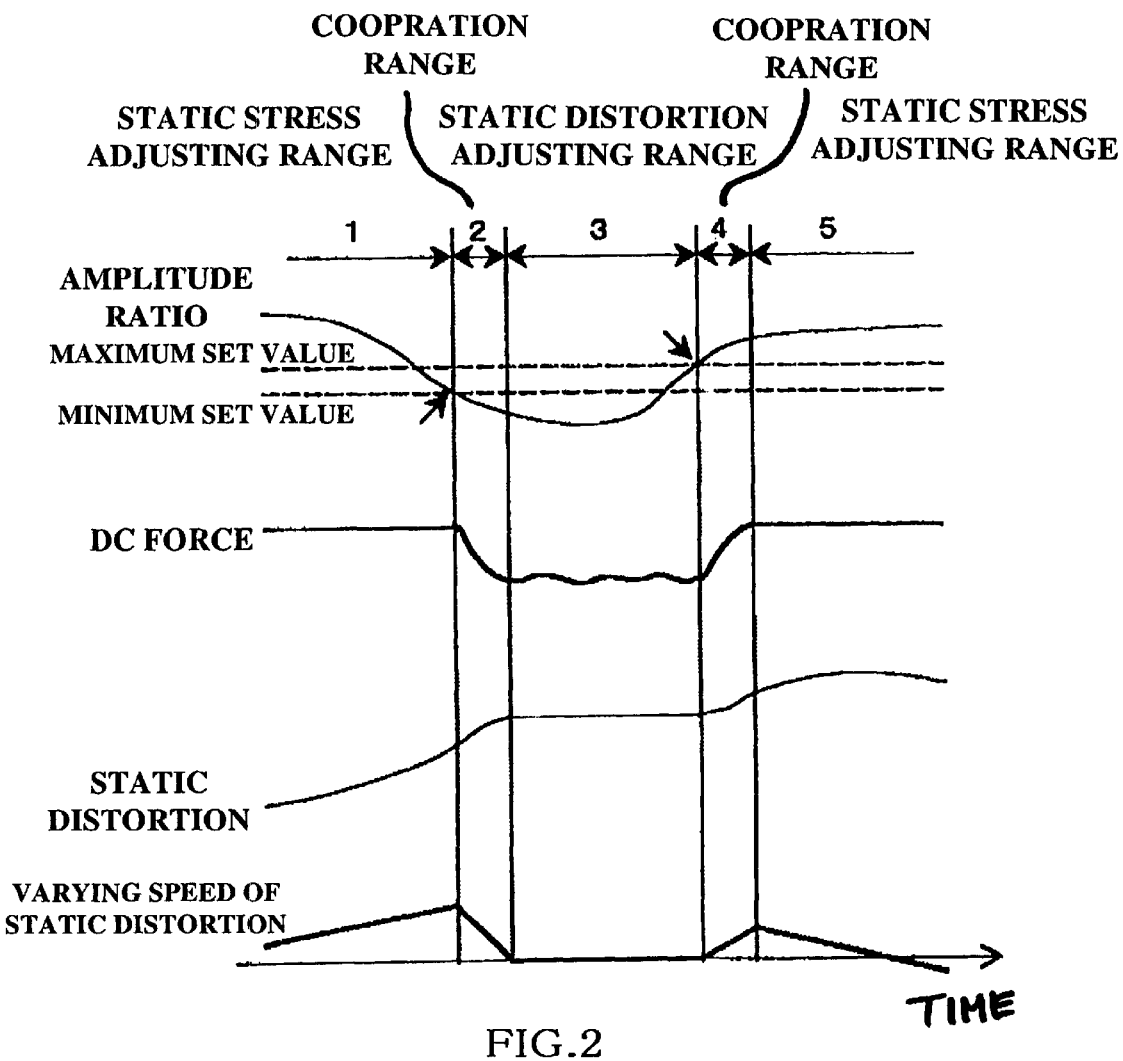
FIG. 2 schematically shows the concept of varying speeds of static distortion, and DC force.

FIG. 2 schematically shows the concept of the selective operation and cooperation of the static distortion adjuster and the static stress adjuster. The abscissa denotes time, and the ordinate denotes: an amplitude ratio of AC force amplitude to distortion amplitude; DC force applied to the specimen; static distortion derived by time-averaging step-by-step positions of the moving mechanism; and varying speed of the static distortion derived by time-differentiating the time-averaged position of the moving mechanism.

Referring to FIG. 2, in the range 1, since the specimen remains stiff and the amplitude ratio is above the minimum value, the DC force applied to the specimen is adjusted to zero by the static stress adjuster. Although the distortion signal is subject to offset due to a warp caused by the thermal expansion of the specimen and residual stress, the offset adjusting circuit operates to move the moving mechanism, and quickly eliminates the offset. As a result, the static distortion is varying.

In the range 2 shown in FIG. 2, the specimen becomes soft and the amplitude ratio is below the minimum value. This state is a transient state which is present until the varying speed of the static distortion becomes zero after the moving mechanism is stopped. If the moving mechanism were abruptly stopped, discontinuous noise or the like might occur in data of the measured viscoelasticity. Therefore, the varying speed is gradually reduced to zero. In this state, the static distortion adjuster and the static stress adjuster are in cooperation.

Referring to FIG. 2, the amplitude ratio remains above the maximum value in the range 3. Therefore, the moving mechanism remains immovable by the static distortion adjuster, and the varying speed of the static distortion is zero. In order to make the offset of the distortion signal zero, the DC force is finely controlled.

In the range 4, the DC force applied to the specimen is being returned to zero since the specimen becomes stiff and the amplitude ratio becomes larger than the maximum value. If the DC force were abruptly returned to zero, discontinuous noise or the like might be caused in data of the measured viscoelasticity. In order to prevent this phenomenon, the DC force is being gradually returned to zero. Therefore, both the static distortion adjuster and the static stress adjuster cooperate in the range 4.

The range 5 is identical to range 1.

There is a difference between the maximum and minimum set values in order to provide an insensitive zone, for the following reasons. If the maximum and minimum set values are equal, and if a state of the specimen remains near these set values, a repeated control state is interrupted, the varying speed of the static distortion and the DC force become very unstable, and the specimen may undergo unnecessarily creep and so on.

In this embodiment, in the ranges 1, 3 and 5, the circuit 28 adjusts either the varying speed of the static distortion of the DC force to zero, by selectively operating the static stress adjuster or the static distortion adjuster. In the ranges 2 and 4, either the varying speed of the static distortion of the DC force is adjusted to a small value which is not zero, which means that both the static stress and distortion adjusters are cooperating.

In the range 2, the DC force is varied in order to gradually return the varying speed of the static distortion to zero. A maximum value is determined for an absolute value of the varying speed of the DC force. Further, the varying speed of the DC force is controlled to be high when the varying speed of the static distortion is high. Conversely, the varying speed of the DC force is controlled to be low when the varying speed of the static distortion is low. Therefore, it takes time to reach the reliable state in the region 5, which is effective in suppressing abrupt variations of the static distortion.

An actual measuring system is required not only to adjust the static distortion or the static stress in accordance with a predetermined program which enables the static distortion or stress to have a certain value or vary linearly, but also to have functions which enable the static distortion adjuster and the static stress adjuster to cooperate depending upon statuses of the specimen and gradually stabilize the static distortion or the static stress.

When the control operation applied to the ranges 2 and 4 is applied to the range 3, it is possible to adjust the varying speed of the static distortion and the DC force to certain minute values including zero, or adjust them such that they have an optional functional relationship.

As described above, the dynamic viscoelasticity measuring system applies the prior art technology to dynamic viscoelasticity measurement of the bending or shearing type, is provided with the selective operation/cooperation determining unit for selectively operating either the static distortion adjuster for adjusting the static distortion occurring in the specimen or the static stress adjuster for adjusting the static stress in the specimen, or operates both the static stress and distortion adjusters, depending upon quality change of the specimen being measured. Therefore, it is possible to eliminate influences such as the warp caused by the terminal expansion of the specimen or residual stress. Further, it is possible to maintain the moving mechanism immovable at the initial position even when the specimen has little restoring force. This prevents the specimen from being excessively distorted, and makes it possible to maintain ideal bending deformation of shearing deformation.

What is claimed is:

1. A dynamic viscoelasticity measuring system for measuring viscoelasticity of a specimen on the basis of a relationship between AC stress and AC distortion occurring in the specimen, comprising: static distortion adjusting means for adjusting static distortion generated in the specimen; static stress adjusting means for adjusting static stress generated in the specimen; and means for selectively operating either one of the static distortion adjusting means or the static stress adjusting means or operating both of the static distortion adjusting means and the static stress adjusting means coopertively to measure dynamic viscoelasticity depending upon quality changes of the specimen being measure.

2. The system of claim 1; wherein the means for selectively operating determines whether to operate one or both of the static distortion adjusting means and the static stress adjusting means on the basis of a ratio of the AC stress to the AC distortion which reflects elasticity of the specimen.

3. The system of claim 1; wherein the means for selectively operating determines whether to operate one or both of the static distortion adjusting means and the static stress adjusting means on the basis of a varying speed of the static distortion occurring in the specimen.

4. The system of claim 1; further comprising means for controlling one of the static distortion adjusting means to adjust the varying speed of the static distortion to zero or the static stress adjusting means to adjust the static stress to zero to measure viscoelasticity of the specimen.

5. The system of claim 4; further comprising means for performing viscoelasticity measurement by operating both of the static distortion adjusting means and the static stress adjusting means until the static stress is reduced to zero when the static distortion adjusting means is switched over to the static stress adjusting means.

6. The system of claim 4; further comprising means for performing viscoelasticity measurement by operating both of the static distortion adjusting means and the static stress adjusting means until the varying speed of the static distortion is reduced to zero when the static stress adjusting means is switched over to the static distortion adjusting means.

* * * * *